(12) United States Patent
Albanese et al.

(10) Patent No.: US 10,835,699 B2
(45) Date of Patent: Nov. 17, 2020

(54) SYSTEMS AND METHODS FOR MODEL-BASED OPTIMIZATION OF MECHANICAL VENTILATION

(71) Applicant: KONINKLIJKE PHILIPS N.V., Eindhoven (NL)

(72) Inventors: Antonio Albanese, New York, NY (US); Nicolas Wadih Chbat, White Plains, NY (US); Roberto Buizza, Boston, MA (US); Nikolaos Karamolegkos, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 291 days.

(21) Appl. No.: 15/538,245

(22) PCT Filed: Dec. 21, 2015

(86) PCT No.: PCT/IB2015/059819
§ 371 (c)(1),
(2) Date: Jun. 21, 2017

(87) PCT Pub. No.: WO2016/103142
PCT Pub. Date: Jun. 30, 2016

(65) Prior Publication Data
US 2018/0001042 A1    Jan. 4, 2018

Related U.S. Application Data (60) Provisional application No. 62/096,100, filed on Dec. 23, 2014.

(51) Int. Cl.
| | |
|---|---|
| *A61M 16/00* | (2006.01) |
| *G16H 50/50* | (2018.01) |
| *G06F 19/00* | (2018.01) |
| *G16H 40/63* | (2018.01) |
| *G05B 17/02* | (2006.01) |

(52) U.S. Cl.
CPC ...... *A61M 16/026* (2017.08); *A61M 16/0057* (2013.01); *G05B 17/02* (2013.01);
(Continued)

(58) Field of Classification Search
CPC .............. A61M 16/026; A61M 16/022; A61M 16/024; A61M 2205/502; A61M 2205/52;
(Continued)

(56) References Cited

U.S. PATENT DOCUMENTS

| | | |
|---|---|---|
| 8,544,466 B2 | 10/2013 | Blanch et al. |
| 8,728,002 B2 | 5/2014 | Al-Rawas et al. |

(Continued)

FOREIGN PATENT DOCUMENTS

| | | |
|---|---|---|
| CN | 202526731 U | 11/2012 |
| WO | 2013144925 A1 | 10/2013 |

OTHER PUBLICATIONS

Rees, S.E., Allerød, C., Murley, D. et al., Using Physiological Models and Decision Theory for Selecting Appropriate Ventilator Settings, J Clin Monit Comput (2006) 20: 421. https://doi.org/10.1007/s10877-006-9049-5 (Year: 2006).*

(Continued)

*Primary Examiner* — Bradley H Philips
*Assistant Examiner* — Savannah L Gabriel
(74) *Attorney, Agent, or Firm* — Daniel H. Brean (57) ABSTRACT

A mechanical ventilator (10) is connected with a ventilated patient (12) to provide ventilation in accordance with ventilator settings of the mechanical ventilator. Physiological values (variables) are acquired for the ventilated patient using physiological sensors (32). A ventilated patient cardiopulmonary (CP) model (40) is fitted to the acquired physiological variables values to generate a fitted ventilated patient CP model by fine-tuning its parameters (50). Updated ventilator settings are determined by adjusting
(Continued)

model ventilator settings of the fitted ventilated patient CP model to minimize a cost function (60). The updated ventilator settings may be displayed on a display component (22) as recommended ventilator settings for the ventilated patient, or the ventilator settings of the mechanical ventilator may be automatically changed to the updated ventilator settings so as to automatically control the mechanical ventilator.

18 Claims, 2 Drawing Sheets (52) U.S. Cl.
CPC ......... *G06F 19/3481* (2013.01); *G16H 40/63* (2018.01); *G16H 50/50* (2018.01); *A61M 2016/003* (2013.01); *A61M 2016/0027* (2013.01); *A61M 2202/0208* (2013.01); *A61M 2205/3303* (2013.01); *A61M 2205/3344* (2013.01); *A61M 2205/502* (2013.01); *A61M 2230/04* (2013.01); *A61M 2230/205* (2013.01)

(58) Field of Classification Search
CPC ........... A61M 2205/3334; G16H 40/63; G05B 17/02; G06F 19/00; A61B 5/4836; A61B 5/087
See application file for complete search history.

(56) References Cited

U.S. PATENT DOCUMENTS

| 10,631,792 | B2 | 4/2020 | Pinsky |
| 2003/0221689 | A1 | 12/2003 | Berthon-Jones |
| 2007/0000494 | A1* | 1/2007 | Banner ............... A61B 5/0205 128/204.23 |
| 2012/0330177 | A1 | 12/2012 | Al-Rawas et al. |
| 2013/0284172 | A1* | 10/2013 | Doyle ............... A61M 16/0051 128/204.23 |

OTHER PUBLICATIONS

Miller, Lachlan, Understanding and Calculating the Cost Function for Linear Regression, May 4, 2018 (Year: 2018).*
Grossbach et al: "Overview of Mechanical Ventilatory Support and Management of Patient- and Ventilator-Related Responses"; Critical Care Nurse, vol. 31, No. 3, Jun. 2011, pp. 30-45.
Mireles-Cabodevila et al: "A Rational Framework for Selecting Modes of Ventilation"; Respiratory Care, Feb. 2013, vol. 58, No. 2, pp. 348-366.
Woodruff: "A Quick Guide to Vent Essentials"; Modern Medicine Network, Downloaded From http://www.modernmedicine.com/modern-medicine/content/tags/copd/quick-guide-vent-essentials, on Mar. 30, 20 pp. 1-6.
Chbat et al: "A Comprehensive Cardiopulmonary Simulation Model for the Analysis of Hypercapnic Respiratory Failure"; 31st Annual International Conference of the IEEE EMBS, Minneapolis, Minnesota, Sep. 2009, pp. 5474-5477.
Cheng et al: "An Integrative Model of Respiratory and Cardiovascular Control in Sleep-Disordered Breathing"; Respiratory Physiology & Neurobiology, vol. 174, 2010, pp. 4-28.
Lu et al: "A Human Cardiopulmonary System Model Applied to the Analysis of the Valsalva Maneuver"; Am J Physiol Heart Circ Physiol, vol. 281,, pp. H2661-H2679, 2001.
David W. Woodruff, "A quick guide to vent essentials", Modern Medicine Network, Sep. 2005. http://www.modernmedicine.com/modern-medicine/content/tags/copd/quick-guide-vent-essentials.

* cited by examiner

SYSTEMS AND METHODS FOR MODEL-BASED OPTIMIZATION OF MECHANICAL VENTILATION

CROSS-REFERENCE TO PRIOR APPLICATIONS

This application is the U.S. National Phase application under 35 U.S.C. § 371 of International Application No. PCT/IB2015/059819, filed on Dec. 21, 2015, which claims the benefit of U.S. Provisional Patent Application No. 62/096,100, filed on Dec. 23, 2014. These applications are hereby incorporated by reference herein.

The following relates to the respiratory therapy arts, respiratory monitoring arts, medical ventilation arts, and related arts.

Mechanical ventilation (MV) is a commonly-used lifesaving procedure, which is administered when a patient is not able to achieve adequate ventilation (and thereby gas exchange) by spontaneous breathing. In passive patient ventilation, the patient is unable to assist in breathing, and the ventilator operates in a pressure control mode in which the ventilator pressure performs the entire work of breathing. In active patient ventilation, the patient can at least assist in breathing, and the ventilator operates in a pressure support mode to provide sufficient pressure to overcome any deficiency in the patient's work of breathing (WoB). Volume control modes of ventilator operation are also known, in which flow rate or volume is the controlled parameter, rather than controlling pressure (although pressure limit settings may also be applied to guard against pulmonary barotrauma).

Although mechanical ventilation has been used in critical care settings for many years, it has some disadvantages. Mechanical ventilation exposes the patients' lungs to potentially destructive fluids and mechanical energy. For example, if the air flow is too rich in oxygen (e.g., the fraction of inspired oxygen, $FiO_2$ is set too high) for a given patient, this can lead to lung-damaging oxygen toxicity. The mechanical energy can lead to ventilator-induced lung injury (VILI) if flow rates or pressures are excessive for the given patient. Such lung damage due to the ventilator can exacerbate existing conditions, prolong length of stay in the critical care unit, and increase the risk of infection, pneumonia, and fatality.

Thus, one of the main challenges in mechanical ventilation is selecting the appropriate ventilation mode and adjusting the ventilator settings as the conditions or the status of the patient change. Unfortunately, the effects of mechanical ventilation on the patient status are difficult to predict, and the ventilator settings may need to be adjusted over the course of the patient's ventilation therapy. Moreover, the various ventilator settings can have both positive and detrimental effects, requiring careful balancing by the doctor or respiratory therapist. For example, in order to improve patient oxygenation, the level of oxygen gas fraction in the inspired air ($FiO_2$) may be increased; however, an elevated $FiO_2$ level may prove to be toxic for the patient. Similarly, in order to increase the amount of air that goes into the patient's lungs per breath, the inspiratory pressure may be increased (if in pressure control mode) or the tidal volume may be increased (if in volume control mode). However, increasing the inspiratory pressure setting may lead to barotrauma, while increasing the tidal volume setting may lead to volutrauma.

Initial ventilator settings are commonly chosen based on the medical expertise of the physician or respiratory therapist, and are thereafter adjusted on a trial-and-error basis as the ventilated patient response is observed. Such an approach is reactive by nature, and may fail to correct a sub-optimal ventilator setting before patient injury occurs. Standardized ventilator management protocols and guidelines are also sometimes employed. However, these protocols and guidelines are not tailored to the specific patient's pathophysiology, and the patient may therefore be ventilated with sub-optimal settings even if the protocols or guidelines are properly adhered to.

The following provides new and improved systems and methods which overcome the foregoing problems and others.

In accordance with one aspect, a medical ventilator system comprises: a mechanical ventilator connected with a ventilated patient to provide ventilation to the ventilated patient in accordance with ventilator settings; physiological sensors configured to acquire measured values for the ventilated patient of monitored physiological variables; a cardiopulmonary (CP) modeling component comprising a microprocessor programmed to generate computed values for the ventilated patient of unmonitored physiological parameters based on the measured values for the ventilated patient of the monitored physiological variables and the ventilator settings; and a ventilator optimization component comprising a microprocessor programmed to output updated ventilator settings based on the measured values for the ventilated patient of the monitored physiological variables, the computed values for the ventilated patient of the unmonitored physiological parameters, and one or more physiological parameter constraints.

In accordance with another aspect, a non-transitory storage medium stores instructions readable and executable by one or more microprocessors to perform a method in conjunction with a mechanical ventilator connected with a ventilated patient to provide ventilation in accordance with ventilator settings of the mechanical ventilator. The method performed by executing the stored instructions comprises: acquiring physiological variable values for the ventilated patient from physiological sensors; fitting a ventilated patient cardiopulmonary (CP) model to the acquired physiological variable values to generate a fitted ventilated patient CP model; and determining updated ventilator settings by adjusting model ventilator settings of the fitted ventilated patient CP model to minimize a cost function.

In accordance with another aspect, a mechanical ventilation method is disclosed. Ventilation is provided to a ventilated patient using a mechanical ventilator in accordance with ventilator settings of the mechanical ventilator. Physiological variable values including at least airway flow rate and airway pressure are acquired using physiological sensors monitoring the ventilated patient. A ventilated patient cardiopulmonary (CP) model is fitted to the acquired physiological variable values to generate a fitted ventilated patient CP model. Updated ventilator settings are determined by adjusting model ventilator settings of the fitted ventilated patient CP model to minimize a cost function. The updated ventilator settings are displayed as recommended ventilator settings for the ventilated patient. Additionally or alternatively, the ventilator settings of the mechanical ventilator are automatically changed to the updated ventilator settings.

One advantage resides in providing patient ventilation with improved therapeutic value.

Another advantage resides in providing patient ventilation with reduced risk of injury to the patient.

Another advantage resides in providing a mechanical ventilator system with an improved operator user interface that is easier to use, more efficient, and less prone to user error.

Another advantage resides in providing a mechanical ventilator system that automatically adjusts its ventilator settings in response to a change in patient condition, or that provides recommendations for such adjustment via a user interface of the ventilator.

Further advantages of the present invention will be appreciated to those of ordinary skill in the art upon reading and understand the following detailed description. It will be appreciated that any given embodiment may achieve none, one, more, or all of the foregoing advantages and/or may achieve other advantages.

The invention may take form in various components and arrangements of components, and in various steps and arrangements of steps. The drawings are only for purposes of illustrating the preferred embodiments and are not to be construed as limiting the invention.

Figure 1:
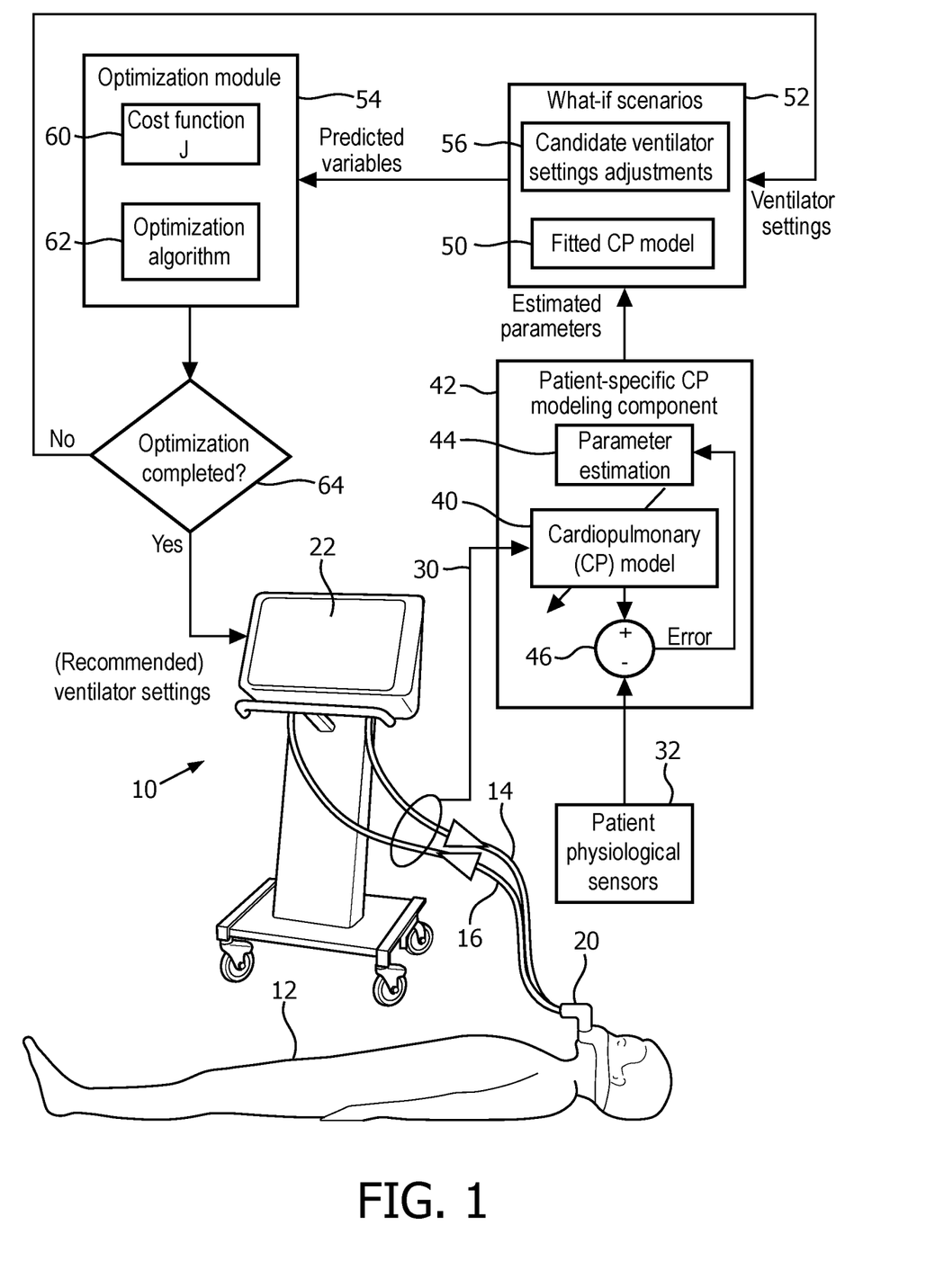
FIG. 1 diagrammatically shows a medical ventilation system.

With reference to FIG. 1, a medical ventilator system includes a mechanical ventilator 10 that delivers air flow in accordance with ventilator settings to a ventilated patient 12 via an inlet air hose 14. Exhaled air returns to the ventilator 10 via an exhalation air hose 16. A Y-piece or T-piece 20 couples air from the discharge end of the inlet air hose 14 to the ventilated patient 12 during inhalation and couples exhaled air from the ventilated patient 12 into the exhalation air hose 16 during exhalation. Not shown in FIG. 1 are numerous other ancillary components that may be provided depending upon the ventilation mode and other therapy being received by the ventilated patient 12. Such ancillary components may include, by way of illustration: an oxygen bottle or other medical-grade oxygen source for delivering a controlled level of oxygen to the air flow, usually controlled by a Fraction of Inspired Oxygen ($FiO_2$) ventilator setting; a humidifier plumbed into the inlet line 14; a nasogastric tube to provide the patient 12 with nourishment; and so forth. The mechanical ventilator 10 has a user interface including, in the illustrative example, a touch-sensitive display component 22 via which the physician, respiratory specialist, or other medical personnel can enter or adjust the ventilator settings and monitor measured physiological variables and operating parameters of the mechanical ventilator 10. Additionally or alternatively, the user interface may include physical user input controls (buttons, dials, switches, et cetera), a keyboard, a mouse, audible alarm device(s), indicator light(s), or so forth.

FIG. 1, upper portion, diagrammatically illustrates a system for recommending, or directly applying, optimal ventilator settings to satisfy specific therapeutic goals for the ventilated patient 12 set by the caregiver (clinicians or respiratory therapists). The ventilator settings optimization system receives, as inputs, ventilator output information 30, either directly measured or known from the ventilator settings, such as a controlled pressure and/or controlled air flow applied to the air way via Y-piece 20. The ventilator settings optimization system further receives, as input, measured values for the ventilated patient 12 of physiological variables that are monitored by patient physiological sensors 32. These sensors 32 may include, by way of illustration, a flowmeter measuring air way flow rate (e.g. at the Y-piece 20); a pressure gauge measuring air way pressure; and a capnograph measuring carbon dioxide ($CO_2$) in respiration gases, for example, outputting the end-tidal $CO_2$ denoted herein as $EtCO_2$. These variables are directly associated with the respiration; however, the sensors 32 may further include sensors monitoring physiological variables that are indirectly related to respiration, such as heart rate, blood pressure (e.g. arterial blood pressure, central venous pressure, et cetera), and oxygen saturation (e.g. $SpO_2$ level).

The ventilator settings optimization system is based on a physiological model of the cardiopulmonary system of a ventilated patient, referred to herein as a ventilated patient cardiopulmonary (CP) model 40. The ventilated patient CP model 40 suitably incorporates various physiological features, such as cardiovascular circulation, respiratory mechanics, tissue and alveolar gas exchange, short-term neural control mechanisms acting on the cardiovascular and/or respiratory functions, or so forth. In general, the ventilated patient CP model 40 may include some or all of these physiological features, and may optionally include other physiological features. Various physiological models of the heart and lungs can be employed as the ventilated patient CP model 40. Some suitable CP models are described, for example, in: Lu et al., "A human cardiopulmonary system model applied to the analysis of the valsalva maneuver", *Am J Physiol Heart Circ Physiol*, 281:H2661-H2679, 2001; Cheng et al., "An integrative model of respiratory and cardiovascular control in sleep-disordered breathing", *Respir Physiol Neurobiol*, 174:4-28, 2010; and Chbat et al., "A Comprehensivve Cardopulmonary Simulation Model for the Analysis of Hypercapnic Respiratory Failure", 31$^{st}$ Annual Int'l Conf of the IEEE EMBS (Minneapolis, Minn., USA, Sep. 2-6, 2009). The ventilated patient CP model 40 includes aspects simulating the ventilator (i.e. a ventilator model aspect), for example a controlled pressure applied to the airway by the mechanical ventilator 10 via the Y-piece 20 and inlet hose 14 can be modeled as an external ventilator pressure source applied to a resistance representing the larynx (see Chbat et al, supra), while a controlled air flow applied to the airway by the ventilator 10 can be similarly modeled as an external flow source.

The ventilated patient CP model 40 provides a substantial advantage, in that it can be used to generate computed values for the ventilated patient 12 of unmonitored physiological parameters (that is, physiological parameters that are not directly monitored by the sensors 32) based on the values measured by the sensors 32 for the ventilated patient 12 of the monitored physiological variables, and also based on the ventilator settings since these are also inputs to the ventilated patient CP model 40. Another advantage of the ventilated patient CP model 40 is that it can predict patient response to changes in the ventilator settings, as the ventilated patient CP model 40 models interrelationships between the ventilator settings and the various physiological parameters.

With continuing reference to FIG. 1, the ventilated patient CP model 40 is personalized in real-time by a patient-specific CP modelling component 42 to fit the specific ventilated patient 12. A parameter estimation algorithm 44 is applied to adapt the CP model to the patient's changing conditions based on physiological variable measurements collected from the patient 12 by the sensors 32. A comparator component 46 determines the error between (1) predictions of the ventilated patient CP model 40 for the monitored physiological variables and (2) the values for the ventilated patient 12 of the monitored physiological variables as measured by the sensors 32. The criterion used in the parameter estimation routine 44 is the minimization of this error. The output of the patient-specific CP modelling component 42 is a fitted ventilated patient CP model 50 that is then used by a ventilator optimization component 52, 54 to optimize the ventilator settings. In the illustrative example of FIG. 1, the ventilator optimization component 52, 54 includes a "what-if" scenarios module 52 and an optimization module 54 that operate as described next.

The what-if scenarios module 52 uses the fitted ventilated patient CP model 50 to assess the impact of various candidate ventilator settings adjustments 56. The optimization module 54 computes a cost function 60 for each such adjustment and applies an optimization algorithm 62 (e.g. a space search, or a more complex optimization such as gradient descent) to identify an optimal ventilator settings adjustment. More particularly, the what-if scenarios module 52 makes each candidate ventilator settings adjustment 56 to the fitted ventilated patient CP model 50 to predict a patient response to the adjustment, and the optimization module 54 computes the value of the cost function 60 for the fitted ventilated patient CP model with the candidate ventilator settings adjustment based on the predicted patient response. The cost function 60 represents an aggregate cost associated with each candidate ventilator settings adjustment. (Note that "cost" as used herein also encompasses benefit, e.g. the cost function 60 may be constructed so that a ventilator system adjustment predicted to actually aggregate the condition of the ventilated patient 12 produces a low cost, or even a negative cost depending upon the cost function design). The cost function 60 is defined by aggregating cost terms so as to take into account benefits or costs such as model-predicted deviations from therapeutic goals set by the caregiver (e.g. arterial $O_2$ and $CO_2$ blood content goals, and/or goals related to minimizing or avoiding detrimental effects such as oxygen toxicity, alveolar pressure, and so forth. It will be appreciated that some cost terms may be inherently statistical in nature, e.g. a barotrauma cost term may quantify the risk (in terms of likelihood of occurrence and/or likely severity) of barotrauma. In one illustrative embodiment the cost function 60 includes cost terms representing barotrauma (a risk/cost), oxygenation (a benefit/goal), $CO_2$ removal (a benefit/goal), and oxygen toxicity (a risk/cost). In another illustrative embodiment the cost function 60 includes these cost terms as well as additional cost terms representing tissue perfusion (a benefit/goal) and hypotension (a risk/cost). The optimization algorithm 62 searches the candidate ventilator setting adjustments 56 to determine the ventilator settings adjustment for recommendation or implementation that minimizes the cost function 60 with respect to the set of candidate ventilator settings adjustments 56. In an optional decision operation 64, the output ventilator setting adjustment is analysed for suitability or appropriateness. For example, if the optimization module 62 employs a simple grid search over a set of candidate ventilator settings adjustments 56 spanning some region of the settings space, and the determined optimal ventilator settings adjustment lies at an edge of that region of the settings space, then process flow may return to the what-if scenarios component 52 in order to shift the search grid to an adjacent region of the settings space (the rationale here is that the grid search finding an edge value suggests the true optimum is outside of the search region). As another example, the decision operation 64 may verify that the determined optimal ventilator settings adjustment actually lies within the range of settings that can be assumed by the mechanical ventilator 10, and/or may verify that the optimal ventilator settings adjustment does not violate some patient ventilation guideline employed at the medical institution.

In addition to minimizing the cost function 60, the optimization performed by the optimization algorithm 62 may be a constrained optimization in which the optimization is constrained by one or more physiological parameter constraints specified by the physician or other medical personnel. For example, one such constraint may require that arterial blood oxygen partial pressure ($PaO_2$) lie within a physician-specified range, and/or that the arterial blood carbon dioxide partial pressure ($PaCO_2$) lie within a physician-specified range. Advantageously, these are high-level therapeutic goals of interest to the physician—the constrained optimization then ensures that the optimal ventilator settings achieve these high-level therapeutic goals while also optimizing with respect to the benefits/costs represented by terms of the cost function 60.

The determined ventilator settings adjustment serves as updated ventilator settings that may be variously used. In one approach, the ventilator display component 22 is configured to display the updated ventilator settings as recommended ventilator settings for the ventilated patient 12. This approach is referred to herein as an "open loop" operating mode, because the ventilator settings optimization system does not actually control the mechanical ventilator 10, but rather provides recommendations as to ventilator setting adjustments that may improve the patient ventilation. The physician, respiratory specialist, or other medical personnel is then free to use professional judgement as to whether the recommendation should actually be implemented—if so, then the medical personnel operate the user interface 22 (e.g. touch-screen display) to change the settings. In a variant embodiment of the open-loop configuration, the display of the recommended settings includes an associated "accept" soft-key that, if selected by medical personnel via the touch-screen display, applies the recommended ventilator settings adjustment. This can be especially useful if the recommended adjustment includes adjusting several different ventilator settings, as they can all be applied by pressing the single "accept" soft-key.

In a closed-loop operating mode, the optimal ventilator settings adjustment is automatically applied without intervention of medical personnel. This approach advantageously enables very rapid (essentially real-time) response to a sudden change in the condition of the ventilated patient 12. However, the physician may be concerned about having the ventilator settings be changed automatically without the physician's oversight. One way to address this concern is to include upper and/or lower limits on various ventilator settings—these limits are then constraints of the constrained optimization performed by the optimization algorithm 62.

The various data processing components 42, 52, 54, 64 of the ventilator settings optimization system are suitably implemented as a microprocessor programmed by firmware or software to perform the disclosed operations. In some embodiments, the microprocessor is integral to the mechanical ventilator 10, so that the data processing is directly performed by the ventilator 10. This has the advantage that the ventilator settings optimization system benefits from the failsafe mechanisms of the mechanical ventilator 10 (e.g. battery backup or other continuous power provisions, redundancy, et cetera).

In other embodiments the microprocessor is separate from the mechanical ventilator 10, for example being the microprocessor of a desktop computer connected with the ventilator 10 by a USB cable, wireless connection, or the like. In such embodiments, the microprocessor is not necessarily classed as a life-critical system, e.g. may not have continuous power provisions or the like. For operation in open-loop mode this is not problematic since failure of the ventilator settings optimization system merely results in not providing ventilator setting adjustment recommendations. For operation in closed-loop mode some provision is preferably made for possible failure of the ventilator settings optimization system. For example, in the absence of a control signal to the ventilator 10 from the ventilator settings optimization system, the ventilator 10 may be designed to return to open-loop operation. The ventilator 10 typically also has built-in ventilator setting limits.

The various data processing components 42, 52, 54, 64 of the ventilator settings optimization system may also be implemented as a non-transitory storage medium storing instructions readable and executable by a microprocessor (e.g. as described above) to implement the disclosed ventilator settings optimization operations. The non-transitory storage medium may, for example, comprise a read-only memory (ROM), programmable read-only memory (PROM), flash memory, or other repository of firmware for the ventilator 10. Additionally or alternatively, the non-transitory storage medium may comprise a computer hard drive (suitable for computer-implemented embodiments), an optical disk (e.g. for installation on such a computer), a network server data storage (e.g. RAID array) from which the ventilator 10 or a computer can download the system software or firmware via the Internet or another electronic data network, or so forth.

In the following, some further illustrative embodiments of various components of the ventilator settings optimization system are described in further detail.

The parameter estimation component 44 fits the ventilated patient CP model 40 to generate a fitted model providing a representation of the specific patient 12 being provided with ventilation by the ventilator 10. The model parameters, which represent physical properties of the cardiopulmonary system (such as respiratory system resistance, chest wall compliance, ventricular contractility, et cetera) are tuned, i.e. fitted to the patient 12 as characterized by the physiological variables measurements provided by the sensors 32. In one suitable approach, a Least-Squares estimation algorithm is applied, where the main model's generated output variables (such as blood pressure, heart rate, oxygen saturation, airway pressure and flow, et cetera) are compared with the corresponding patient's measurements (corresponding blood pressure, heart rate, oxygen saturation, airway pressure and flow, et cetera measurements) and the resulting errors output by the comparator 46 are used as a metric to adjust the model's parameters.

The what-if scenarios module 52 then uses the resulting parameters in what-if scenarios routines. Each "what-if" scenario is represented by a candidate ventilator settings adjustment, so that the set of candidate ventilator settings adjustments 56 represent the "what-if" scenarios to be tested. The fitted ventilated patient CP model 50 is adjusted in accord each candidate ventilator settings adjustment, and simulation is repeated for each such candidate settings adjustment, to predict how the specific ventilated patient 12 would respond to each what-if scenario.

At the optimization module 54, for each candidate ventilator settings adjustment, the model-predicted variables are used to build an instance of the cost function 60, denoted herein as cost function J. In an illustrative example, the cost function J takes into account the level of oxygenation and $CO_2$ removal, as well as the risks of barotrauma, oxygen toxicity, hypotension and reduced cardiac output associated with a particular set of ventilator settings (i.e. the candidate ventilator settings adjustment) denoted X:

$$J(X) = \underbrace{f_1(P_{ALV}(X))}_{barotrauma} + \underbrace{f_2(P_{aO2}(X))}_{oxygenation} +$$

$$\underbrace{f_3(P_{aCO2}(X))}_{CO_2\ removal} + \underbrace{f_4(CO(X))}_{tissue\ perfusion} + \underbrace{f_5(ABP(X))}_{hypotension} + \underbrace{f_6(F_{iO2}(X))}_{oxygen\ toxicity}$$

In this illustrative cost function J, the values of the cost function J depend on the particular candidate ventilator settings adjustment represented by the set of ventilator settings X. The arguments of the cost term functions $f_1, \ldots, f_6$ are either measured variables (e.g. ABP may be a measured variables) or are computed values for the ventilated patient 12 of unmonitored physiological parameters (i.e. not measured by the sensors 32) that are computed using the fitted ventilated patient CP model 50 based on the measured values for the ventilated patient of the monitored physiological variables (those monitored by the sensors 32) and the ventilator settings. The various cost term functions $f_1, \ldots, f_6$ are suitably determined from medical literature study data, and/or from heuristic or first-principles analysis of the underlying physiology. For example, the function $f_2$ quantifies the benefit of oxygenation at the quantitative value $PaO_2(X)$, while $f_6$ quantifies the oxygen toxicity cost (risk of occurrence and likely detriment upon occurrence) at the quantitative value $FiO_2(X)$.

The optimization algorithm 62 then minimizes the cost J by with respect to the candidate ventilator settings adjustments X, that is:

$$X_{optimal} = \underset{X}{\operatorname{argmin}}\{J(X)\}$$

In one approach, this is done by an exhaustive space search, e.g. the set of candidate ventilator settings adjustments 56 fills a region of the settings space to be searched, each candidate ventilator settings adjustment X is made to the fitted ventilated patient CP model 50 and the value of a cost function J(X) is computed for the fitted ventilated patient CP model 50 with the candidate ventilator settings adjustment X, and the updated ventilator settings is output as the candidate ventilator settings adjustment X that minimizes the cost function J. In more elaborate approaches, an optimization algorithm such as gradient descent is applied, in which derivatives of the cost function J(X) are computed with respect to each ventilator setting (i.e., with respect to each dimension of the vector X) and these derivatives are used to identify, e.g. via a gradient descent step, a best direction in the settings space to move to locate a more optimal settings adjustment, and this process is iterated until a termination condition is met, e.g. the computed derivatives of J(X) become sufficiently small, or the iteration-to-iteration improvement in J(X) becomes sufficiently small.

To provide further illustration, some more specific embodiments of the ventilator settings optimization system are next described.

Figure 2:
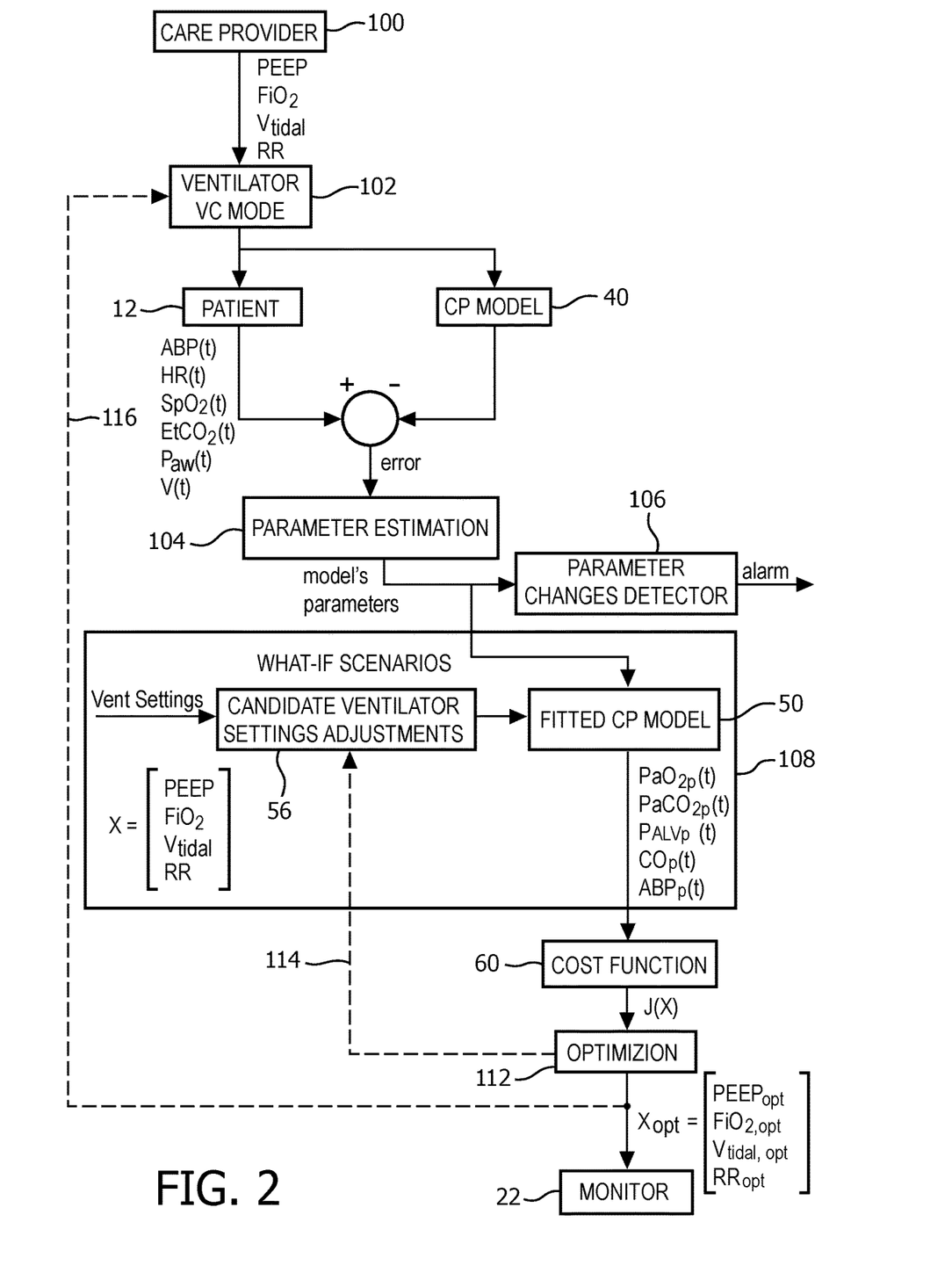
FIG. 2 diagrammatically shows an operations flow chart for the medical ventilation system of FIG. 1.

With reference now to FIG. 2, to provide further illustration, some more specific embodiments of the ventilator settings optimization system are described. In this illustrative embodiment the patient 12 is connected to the ventilator and a caregiver 100 (e.g. a doctor or respiratory therapist) sets up the ventilator in an operation 102 with the ventilation mode chosen by the caregiver being Volume Control (VC). (This is merely an illustrative example, and the disclosed ventilator settings optimization system may be applied to other ventilation modes such as pressure control mode). For the illustrative VC control, the patient is sedated and paralyzed, hence the ventilation is entirely dictated by the ventilator (i.e. passive patient providing no Work of Breathing). The caregiver also assigns initial values for the VC ventilator settings, including: positive end expiratory pressure (PEEP); oxygen gas fraction ($FiO_2$); tidal volume ($V_{tidal}$); and respiratory rate (RR) for this specific patient 12. (Again, in another ventilation mode the ventilator settings may be different from PEEP, $FiO_2$, $V_{tidal}$, and RR). The caregiver 100 takes into account various considerations known to the skilled doctor or respiratory specialist. For example, the caregiver 100 knows that low values of PEEP may cause alveoli units to collapse and hence result in poorly ventilated lungs. On the other hand, high values of PEEP will open up more alveoli units but may impair venous return and hence result in low cardiac output (CO) and mean arterial blood pressure (MAP). Similarly, high values of $FiO_2$ will increase arterial blood oxygen partial pressure ($PaO_2$) but may have toxicity side-effects. Too low values of tidal volume may result in inadequate ventilation, whereas too high tidal volume values may cause volutrauma and barotrauma, depending on the mechanical properties of the patient's lungs. Further, the optimal value of RR to guarantee adequate ventilation will depend upon the chosen tidal volume. It is evident that the simultaneous optimization of the ventilator settings PEEP, $FiO_2$, and RR is a challenging and time-consuming task, and the caregiver 100 understands that improper values for these settings for the specific patient 12 can harm the patient.

By comparison with this challenging and time-consuming task, using the ventilator settings optimization system disclosed herein the caregiver sets approximate initial values for the ventilator settings (here PEEP, $FiO_2$, $V_{tidal}$, and RR), and additionally sets high-level therapeutic goals in terms of $PaO_2$ and $PaCO_2$, such as:

$PaO_2$(desired)=100 mmHg with constraints 80 mmHg<$PaO_2$<150 mmHg $PaCO_2$(desired)=40 mmHg with constraints 10 mmHg<$PaCO_2$<46 mmHg Thereafter, in an operation 104 performed by the ventilator settings optimization system (and more particularly by the patient-specific CP modelling component 42 of FIG. 1), the system automatically optimizes the ventilator settings to get the patient close to these therapeutic goals while minimizing the risks of barotrauma, oxygen toxicity, hypotension and reduced tissue perfusion. These risks are defined with respect to user-selected targets, for example in terms of desired cardiac output (CO), maximum alveolar pressure ($P_{ALV}$) and mean arterial blood pressure (MAP). For instance, the user selected targets can be:

$P_{ALV,max}$=30 mmHg $CO_{desired}$=5 L/min $MAP_{desired}$=100 mmHg

As illustrated in FIG. 2, the first operation 104 comprises personalizing the ventilated patient CP model 40 and performing patient-specific parameter estimation. Here, the ventilated patient CP model 40 initially runs with a default set of parameters—for example, default parameters that are representative of a typical healthy 70 Kg subject. During the parameter estimation 104, the model-generated heart rate (HR), arterial blood pressure (ABP), oxygen saturation ($SpO_2$), end-tidal CO2 ($EtCO_2$), airway pressure ($P_{aw}$) and flow ($\dot{V}$) signals are compared with the corresponding patient measurements, obtained noninvasively via conventional bedside sensors 32 (see FIG. 1). The resulting error (computed by comparator 46) over a specific time window is then minimized according to a Least-Squares algorithm and the model's parameters are adjusted to reflect the patho-physiology of the specific patient 12 receiving mechanical ventilation:

$$\theta^* = \underset{\theta}{\arg\min} \sum_{n=1}^{N} [ABP(n) - ABP_m(n)]^2 + [HR(n) - HR_m(n)]^2 +$$
$$[SpO2(n) - SpO2_m(n)]^2 + +[EtCO2(n) - EtCO2_m(n)]^2 +$$
$$[P_{aw}(n) - P_{aw,m}(n)]^2 + [\dot{V}_{(n)} - \dot{V}_m(n)]^2$$

where the subscript m indicates model generated output variables, N is the length of the time window in which the error is evaluated, n indicates a generic sampling instant within the time window, and $\theta^*$ is the vector containing the patient-specific parameters.

The output of the parameter estimation 104 is the fitted ventilated patient CP model 50 which is personalized to the specific ventilated patient 12. After the model has been personalized, the estimated parameters are stored. If at some time thereafter a parameter changes detector 106 detects a significant change in a parameter, an alarm (visual and/or audible) may be generated to inform the care provider 100 of the change in patient condition. Additionally, the estimated parameters are sent to the what-if scenarios routines 52 performed in operation 108 of FIG. 2. Here, the fitted ventilated patient CP model 50 runs using the estimated parameters. Multiple simulations are performed for different sets of ventilator settings adjustments X as desired by the care provider 100. In a suitable formalism for the illustrative VC mode example, the ventilator settings adjustments X are represented by the following vector notation:

$$X = \begin{bmatrix} PEEP \\ FiO_2 \\ V_{tidal} \\ RR \end{bmatrix}$$

The parameter estimation routine (operation 104) continues running separately in the background, while the what-if scenarios (operation 108) are performed, in order to detect potential changes in patient's health status. The parameter change detector 106 continues to check if the current estimated parameters present substantial deviations from the parameters that have been sent to the what-if scenarios routine 108, in which case an alarm will be generated asking the care provider 100 to restart the what-if scenarios routine 108 because patient's condition has changed.

The model-predicted variables at each simulation run are then used to compute the cost function J according to:

$$J = w_1 \cdot \frac{P_{ALV,p}}{P_{ALV\,max}} + w_2 \cdot \frac{|P_{aO2,p} - P_{aO2\,desired}|}{P_{aO2,max} - P_{aO2,min}} +$$

-continued $$w_3 \cdot \frac{|P_{aCO2,p} - P_{aCO2\ desired}|}{P_{aCO2,max} - P_{aCO2,min}} + + w_4 \cdot |CO_p - CO_{desired}| +$$

$$w_5 \cdot |MAP_p - MAP_{desired}| + w_6 \cdot F_{iO2}$$

where the terms $w_1$, $w_2$, $w_3$, $w_4$, $w_5$ and $w_6$ are weights that can be adjusted by the user in order to prioritize the different therapeutic goals, and the subscript p indicates model-predicted variables. Note that in the computation of the cost function J above, the variables $P_{ALV,p}$, $P_{aO2,p}$ and $P_{aCO2,p}$ are mean quantities over a fixed time window (e.g., one minute).

Finally, given the cost function J, an optimization operation 112 (performed by the optimization module 54 of FIG. 1) searches for the set of ventilator settings that minimizes the cost function J, that is:

$$X_{opt} = \begin{bmatrix} PEEP_{opt} \\ FiO_{2,opt} \\ V_{tidal,opt} \\ RR_{opt} \end{bmatrix}$$

In some embodiments, the optimization operation 112 may loop back to operation 108 in order to test more what-if scenarios (that is, to generate more candidate ventilator settings adjustments), as indicated by a dashed arrow 114. This may arise, for example, if the optimization 112 performs a region search and $X_{opt}$ is found to lie on a boundary of the searched region—in this case the iteration 114 enables the search region to be expanded to investigate whether the optimal solution lies outside of the initial search region. As another example, if the optimization operation employs an iterative approach such as iterative gradient descent, then the iteration 114 enables the gradient step to be followed by producing a new candidate ventilator settings adjustment corresponding to the gradient step.

After the optimal ventilator settings have been computed, they can be displayed on the display device 22 (or more generally, on the ventilator screen 22, on a tablet device, on a desktop computer monitor, or so forth) and provided to the user in the form of suggestions (in the open-loop modality).

If closed loop operation is desired, then the updated ventilator settings $X_{opt}$ are conveyed back to the ventilator as indicated by a dashed loop arrow 116 in FIG. 2. Here the updated ventilator settings $X_{opt}$ are directly applied to the ventilator without a direct consent of the care provider 100. This closed-loop modality does not require the care provider 100 to be physically present to accept the updated ventilator settings.

It should be noted that the volume control (VC) ventilation mode of the illustrative example of FIG. 2 is merely an example. The disclosed ventilator settings optimization system can be applied to other ventilation modes, such as Pressure Control Ventilation (PCV), Pressure Support Ventilation (PSV), Continuous Positive Airway Pressure (CPAP) ventilation, Synchronized Intermittent Mandatory Ventilation (SIMV), and so forth. The ventilator settings to be optimized are not limited to PEEP, $FiO_2$, $V_{tidal}$, and RR, but can be chosen based on the ventilator capabilities and the operating ventilation mode. For instance, other ventilator settings that may be optimized include the inspiratory-to-expiratory time (I:E) ratio, the Inspiratory Time, the PSV level, or so forth. Various ventilated patient CP models can also be used. The measured physiological variables used to fit the ventilated patient CP model is also not limited to the illustrative HR, ABP, $EtCO_2$, $SpO_2$, $P_{aw}$ and $\dot{V}$ variables, but may additionally or alternatively include other physiological variables such as central venous pressure (CVP), laboratory values (pH, $PaO_2$, $PaCO_2$, et cetera), CT and Xray information, or so forth. Techniques other than Least Squares fitting can also be used in the parameter estimation method to fit the model to the measured physiological variables. Other suitable parameter estimation methods include Maximum Likelihood, Maximum a Posteriori Probability, State-Space Identification, and so forth. The therapeutic goals forming the optimization constraints can be different than the illustrative target and bound values for $PaO_2$ and $PaCO_2$. Still further, the cost function J can be constructed in various ways to quantitatively assess the aggregation of desired benefits and risks. For instance, in the case of spontaneous ventilation modalities (CPAP, SIMV), an additional term related to the patient Work of Breathing (WoB) can be added to express the risk of diaphragmatic atrophy/fatigue associated with specific sets of ventilator settings.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical ventilator system comprising:
a mechanical ventilator configured to be connected with a ventilated patient to provide ventilation to the ventilated patient in accordance with a plurality of ventilator settings;
physiological sensors configured to acquire measured values for the ventilated patient of monitored physiological variables;
a cardiopulmonary (CP) modeling component comprising a microprocessor programmed to generate computed values for the ventilated patient of unmonitored physiological parameters, wherein the unmonitored physiological parameters were not measured by sensors, based on the measured values for the ventilated patient of the monitored physiological variables and the plurality of ventilator settings, wherein the CP modeling component is programmed to generate the computed values for the ventilated patient of the unmonitored physiological parameters by operations including:
fitting a ventilated patient CP model to the ventilated patient by fitting predictions of the ventilated patient CP model for the monitored physiological variables to the measured values for the ventilated patient of the monitored physiological variables in order to generate a fitted ventilated patient CP model that is personalized to a specific ventilated patient; and
generating the computed values for the ventilated patient of the unmonitored physiological parameters as the predictions of the fitted ventilated patient CP model for the unmonitored physiological parameters; and
a ventilator optimization component comprising a microprocessor programmed to output updated ventilator settings based on the measured values for the ventilated patient of the monitored physiological variables, the computed values for the ventilated patient of the unmonitored physiological parameters, wherein the ventilator optimization component is programmed to output updated ventilator settings by operations including:

(i) making a candidate ventilator settings adjustment to the fitted ventilated patient CP model and computing a value of a cost function for the fitted ventilated patient CP model with the candidate ventilator settings adjustment, wherein the cost function represents an aggregate cost associated with each candidate ventilator settings adjustment;

(ii) repeating operation (i) for a plurality of different candidate ventilator settings adjustments; and (iii) outputting the updated ventilator settings as the candidate ventilator settings adjustment that minimizes the cost function.

2. The medical ventilator system of claim 1, wherein the cost function includes cost terms representing at least three of barotrauma, oxygenation, $CO_2$ removal, and oxygen toxicity.

3. The medical ventilator system of claim 2, wherein the cost function further includes cost terms representing tissue perfusion and hypotension.

4. The medical ventilator system of claim 1, wherein the ventilator settings include at least two of: positive end expiratory pressure (PEEP), fraction of inspired oxygen ($FiO_2$), tidal volume ($V_{tidal}$), and respiratory rate (RR).

5. The medical ventilator system of claim 1, wherein the monitored physiological variables include at least airway flow rate and airway pressure.

6. The medical ventilator system of claim 5, wherein the monitored physiological variables further include heart rate, blood pressure, and oxygen saturation.

7. The medical ventilator system of claim 1, further comprising:
a ventilator display component configured to display information indicative of the updated ventilator settings output by the ventilator optimization component.

8. The medical ventilator system of claim 1, wherein the mechanical ventilator is configured to automatically update its ventilator settings to the updated ventilator settings output by the ventilator optimization component.

9. A non-transitory storage medium storing instructions readable and executable by one or more microprocessors to cause a mechanical ventilator configured to be connected with a ventilated patient to provide ventilation in accordance with a plurality of ventilator settings of the mechanical ventilator, the one or more microprocessors being instructed to perform steps comprising:
acquiring values of physiological variables for the ventilated patient from physiological sensors;
fitting a ventilated patient cardiopulmonary (CP) model to the acquired values of the physiological variables to generate a fitted ventilated patient CP model that is personalized to a specific ventilated patient;
generating computed values for the ventilated patient of unmonitored physiological parameters as predictions of the fitted ventilated patient CP model for the unmonitored physiological parameters, wherein the unmonitored physiological parameters were not measured by sensors;
determining updated ventilator settings by adjusting candidate ventilator settings of the fitted ventilated patient CP model to minimize a cost function, wherein the cost function represents an aggregate cost associated with each candidate ventilator settings adjustment; and
changing the ventilator settings of the mechanical ventilator to the updated ventilator settings.

10. The non-transitory storage medium of claim 9, wherein the cost function includes cost terms representing barotrauma, oxygenation, $CO_2$ removal, and oxygen toxicity.

11. The non-transitory storage medium of claim 9, wherein the ventilator settings of the mechanical ventilator include: positive end expiratory pressure (PEEP), fraction of inspired oxygen ($FiO_2$), tidal volume ($V_{tidal}$), and respiratory rate (RR).

12. The non-transitory storage medium of claim 9, wherein the acquired physiological variables values include values for at least one of airway flow rate, airway pressure, end-tidal carbon dioxide, heart rate, blood pressure, and oxygen saturation.

13. The non-transitory storage medium of claim 9, wherein the method further comprises:
causing information indicative of the updated ventilator settings to be displayed on a display component as a recommendation for the ventilated patient.

14. The non-transitory storage medium of claim 9, wherein the method further comprises:
causing the ventilator settings of the mechanical ventilator to be automatically changed to the updated ventilator settings whereby the method provides automatic control of the mechanical ventilator.

15. A mechanical ventilation method comprising:
providing ventilation to a ventilated patient using a mechanical ventilator in accordance with a plurality of ventilator settings of the mechanical ventilator;
acquiring physiological variable values including at least airway flow rate and airway pressure using physiological sensors monitoring the ventilated patient;
fitting a ventilated patient cardiopulmonary (CP) model to the acquired physiological variable values to generate a fitted ventilated patient CP model that is personalized to a specific ventilated patient;
generating computed values for the ventilated patient of unmonitored physiological parameters as predictions of the fitted ventilated patient CP model for the unmonitored physiological parameters, wherein the unmonitored physiological parameters were not measured by sensors;
determining updated ventilator settings by adjusting candidate ventilator settings of the fitted ventilated patient CP model to minimize a cost function, wherein the cost function represents an aggregate cost associated with each candidate ventilator settings adjustment; and
at least one of: (i) displaying information indicative of the updated ventilator settings and (ii) automatically changing the ventilator settings of the mechanical ventilator to the updated ventilator settings.

16. The mechanical ventilation method of claim 15, wherein the ventilator settings include fraction of inspired oxygen ($FiO_2$) and at least one of a pressure setting and a volume setting.

17. The mechanical ventilation method of claim 16, wherein one of:
(A) the operation of providing ventilation comprises providing volume control ventilation and the ventilator settings include at least one volume setting; and
(B) the operation of providing ventilation comprises providing pressure control ventilation and the ventilator settings include at least one pressure setting.

18. The mechanical ventilation method of claim 15, wherein the fitting operation further comprises:

fitting the predictions of the ventilated patient CP model for the acquired physiological variables values to the acquired physiological variable values.

\* \* \* \* \*